United States Patent [19]

Tidwell et al.

[11] Patent Number: 4,933,347
[45] Date of Patent: Jun. 12, 1990

[54] DIAMIDINES AND BIS(IMIDAZOLINES) FOR THE TREATMENT OF AND PROPHYLAXIS AGAINST *PNEUMOCYSTIS CARINII* PNEUMONIA

[75] Inventors: Richard R. Tidwell; Dieter J. Geratz, both of Chapel Hill, N.C.; Kwasi A. Ohemeng, Clinton, N.J.; James E. Hall, Chapel Hill, N.C.

[73] Assignee: University of North Carolina at Chapel Hill, Chapel Hill, N.C.

[21] Appl. No.: 262,535

[22] Filed: Oct. 25, 1988

[51] Int. Cl.$^5$ .................. A61K 31/505; C07D 239/06
[52] U.S. Cl. ..................................... 514/256; 514/218; 514/402; 514/636; 540/553; 544/296; 548/350; 564/243
[58] Field of Search ........................ 548/350; 544/296; 540/553; 564/243; 514/402, 256, 218, 636

[56] References Cited

PUBLICATIONS

*Chemical Abstracts,* 96: 135352u (1982), [E. Steck et al., *Exp. Parasitol.* 1981, 52(3), 404–13].
*Chemical Abstracts,* 99: 63892g (1983), [L. Schmidt, *Am. J. Trop. Med. Hyg.,* 1983, 32(2), 231–57].
*Chemical Abstracts,* 102: 40705q (1985), [Austria 538,963, Shaw, 9/6/84].
*Chemical Abstracts,* 71: 20824r (1969), [S. Rasin et al., *Vyssh. Nerv. Deyatel'nost Norme Patol.,* 1967, 2, 93–7].
*Chemical Abstracts,* 83: 22394x (1975), [K. Western et al., *J. Infect. Dis.,* 1975, 131 (3), 267–70].

*Primary Examiner*—Richard A. Schwartz
*Attorney, Agent, or Firm*—Leydig, Voit & Mayer

[57] ABSTRACT

Certain new diamidine and bis(imidazoline) compounds having activity against *Pneumocystis carinii* pneumonia are disclosed along with formulations and methods for treating *Pneumocystis carinii* pneumonia employing said compounds.

14 Claims, No Drawings

DIAMIDINES AND BIS(IMIDAZOLINES) FOR THE TREATMENT OF AND PROPHYLAXIS AGAINST *PNEUMOCYSTIS CARINII* PNEUMONIA

FIELD OF THE INVENTION

This application relates, in general, to methods for treating *Pneumocystis carinii* pneumonia and in particular to new compounds which are pharmaceutically active against *Pneumocystis carinii*, to pharmaceutical formulations containing such compounds, and to methods for the treatment of, and prophylaxis against, *Pneumocystis carinii* pneumonia.

BACKGROUND OF THE INVENTION

Pentamidine, in the form of its hydrochloride salt, was first discovered by Ewins et al., as shown in U.S. Pat. No. 2,277,861, and water-soluble salts were subsequently developed as shown by U.S. Pat. No. 2,410,796 to Newberry et al, which is directed to such water soluble salts, particularly the hydroxy-ethane sulfonic acid and the hydroxy-propane sulfonic acid salts of pentamidine. The former compound is generally referred to as pentamidine isethionate.

Pentamidine isethionate is presently marketed by LyphoMed, Inc. under the trademark Pentam, for intravenous and intramuscular injection, and is indicated for the treatment of pneumonia due to *Pneumocystis carinii*, the latter ailment typically being referred as "PCP". The importance of pentamidine isethionate has dramatically escalated recently due to the marked increase of patients suffering from PCP. The increase in the afflicted patient population is an unfortunate consequence of the increasing presence of the Acquired Immunodeficiency Syndrome ("AIDS"). It is now estimated that approximately 70 percent of AIDS patients contract PCP. Because of the high incidence of PCP in AIDS patients, pentamidine isethionate has found utility not only in the treatment of PCP, but also for prophylaxis, in preventing or delaying the initial onset or recurrence of PCP, especially in AIDS patients.

However, an unfortunate side effect of pentamidine isethionate is its toxicity. Some fatalities have been attributed to severe hypotension, hypoglycemia, and cardiac arrhythmias in patients treated with pentamidine isethionate, through both intramuscular and intravenous routes. Because of the concern over the toxicity of pentamidine isethionate, a severe need has arisen for a replacement for pentamidine isethionate which can avoid or minimize the undesirable side effects associated with the use of pentamidine.

SUMMARY OF THE INVENTION

In accordance with the present invention, surprisingly, it has now been discovered that *Pneumocystis carinii* pneumonia may be effectively treated with certain compounds, as defined in Formula I:

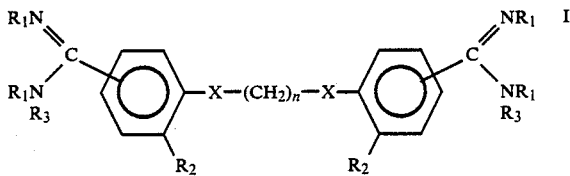

wherein each $R_1$ is H or two $R_1$ groups on the same amidine group together represent $-(CH_2)_m-$, wherein $m=2$, 3, or 4; $R_2$ is H, $OCH_3$, $NO_2$ or $NH_2$; $R_3$ is H, $CH_3$, or $CH_2CH_3$; $n=2$, 3, 4 or 5; and X is 0, N or S; provided that when both $R_1$ and $R_2$ are H and X=O, then n cannot equal 5.

Particularly preferred are those compounds of Formula I which have the para-amidine structure, as shown by Subformula Ia:

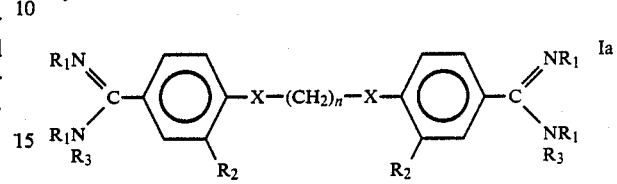

wherein $R_1$, $R_2$, $R_3$, X, m and n have the same meanings as for Formula I.

Many of the compounds which now have been found to be useful in the treatment of, or prophylaxis against, *Pneumocystis carinii* pneumonia are themselves new compounds. Such new compounds are defined by Formula II, as follows:

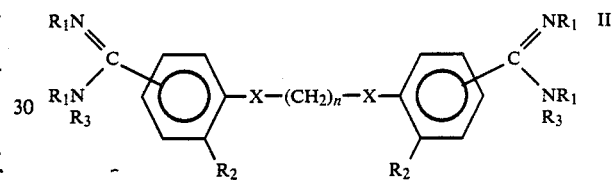

wherein each $R_1$ is H or two $R_1$ groups on the same amidine group together represent $-(CH_2)_m-$, wherein $m=2$, 3 or 4; $R_2$ is H $OCH_3$, $NO_2$or $NH_2$; $R_3$ is H, $CH_3$, or $CH_2CH_3$; $n=2$, 3, 4 or 5; and X is 0, N or S; with the provisos that when both $R_1$ and $R_2$ are H, then X is N or S, and when $R_2$ is H and X is 0, then two $R_1$ groups together represent $-(CH_2)_m-$, and $n=3$ or 4.

Particularly preferred are those compounds of Formula II which have the para-amidine structure, as shown by Subformula IIa:

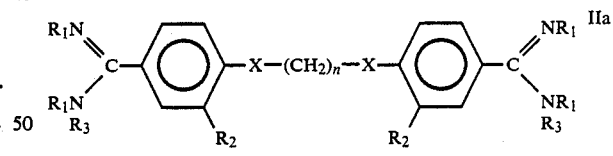

wherein $R_1$, $R_2$, $R_3$, X, m and n and have the same meanings as for Formula II. Additionally, new compounds as otherwise defined in Formula II, but wherein $n=6$ show efficacy against PCP, but have high toxicity.

Generally, the present invention also provides pharmaceutical formulations comprising the aforementioned new compounds of Formula II (or preferably of Formula IIa), or pharmaceutically acceptable salts thereof, in physiologically acceptable carriers. Also, the present invention provides such new compounds or salts thereof which have been lyophilized and which may be reconstituted to form pharmaceutically acceptable formulations for administration, as by intravenous or intramuscular injection.

Further, the present invention provides the aforementioned compounds or salts thereof as formulations for administration as aerosolized particles or droplets for inhalation.

DETAILED DESCRIPTION OF THE INVENTION

The distinguishing structural features between the new compounds of the present invention and those of the prior art are quite apparent, and readily may be ascertained by comparing the structures of such compounds with the structure of pentamidine, which is shown in Formula III:

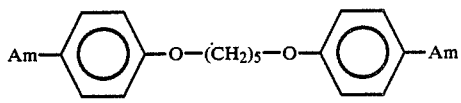

III wherein Am represents an amidine group.

In one aspect of the present invention, the new compounds are distinguishable from pentamidine and previously known analogues thereof, by the presence of a nitrogen or sulfur atom, in place of the etheric oxygens in the group bridging the two aromatic nuclei. Such new compositions are represented by Formula II (or Subformula IIa), wherein X is N or S. In such instances then the novel compounds have the structure of the following general Formula IVa or IVb, or preferably the specific para-amidine structure of Subformula IVc, or IVd:

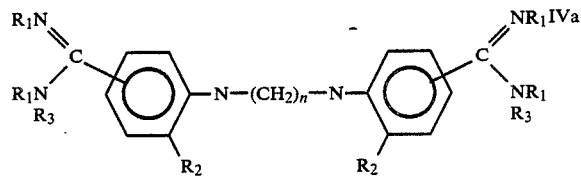

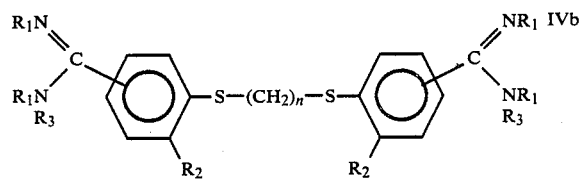

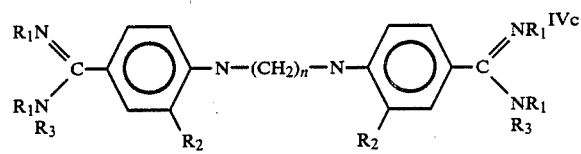

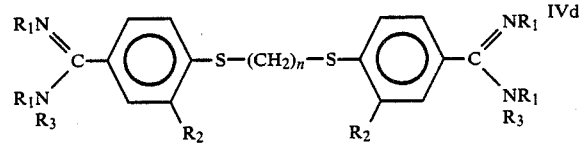

wherein each $R_1$ is H or two $R_1$ groups on the same amidine group together represent $-(CH_2)_m-$, wherein m is 2, 3 or 4; $R_2$ is H, $OCH_3$, $NH_2$ or $NO_2$; $R_3$ is H, $CH_3$ or $CH_2CH_3$; and n=2, 3, 4 or 5. As indicated, no such compositions exist in the prior art in which the link between the two aromatic nuclei is by a group having the formula $-H-(CH_2)_n-N-$ or $-S-(CH_2)_n-S-$, and that feature alone distinguishes the compounds having the Formula IV from those of the prior art.

Another aspect of the present invention distinguishes new compounds of the present invention from the prior art through the presence of a methoxy, an amino or a nitro group on the two aromatic nuclei. Such compositions are represented in Formula II (or preferably in Formula IIa) when $R_2$ is $OCH_3$, $NH_2$ or $NO_2$ and may be represented specifically by Formula V or preferably by the para-amidine structure of Subformula Va:

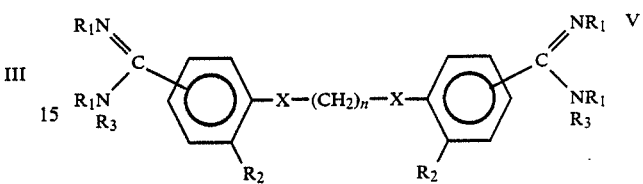

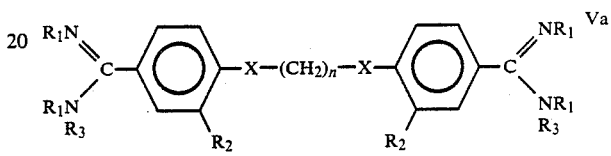

wherein each $R_1$ is H or two $R_1$ groups on the same amidine group together represent $-(CH_2)_m-$, wherein m is 2, 3 or 4; $R_2$ is $OCH_3$, $NH_2$ or $NO_2$; $R_3$ is H, $CH_3$, or $CH_2CH_3$; X is O, N or S; and n=2, 3, 4, or 5. Such compositions then are distinguished from pentamidine and analogues thereof through the presence of the methoxy, amino or nitro group, the methoxy and amino group having been found to increase the therapeutic efficacy of such compounds with respect to their activity against *Pneumocystis carinii*. The methoxy group in particular substantially increases the therapeutic efficacy of the compound.

In a further aspect of the present invention, certain of the new compounds are distinguished from the compounds of the prior art through the existence of closed ring derivatives of the amidine group, such as imidazoline rings, on both of the aromatic nuclei. The closed ring, such as imidazoline, is formed by bridging the nitrogen atoms on both of the amidine groups, through a $-(CH_2)_m$ group, such as $-CH_2CH_2-$. Referring to Formula II then, such compounds are represented when two $R_1$ groups on the same amidine group together represent $-(CH_2)_m$ wherein m=2, 3 or 4. Such compounds are unknown in the art when X is N or S and/or when $R_2$ is $OCH_3$, $NH_2$ or $NO_2$. Further, such compounds are unknown in the art when X is O and n=2, 3 or 4. The imidazoline compound is known, however, when X is O, $R_2$ is H, and n=5. Said compound, however, is not known to have therapeutic efficacy against *Pneumocystis carinii*. However, the presence of the closed ring, such as an imidazoline group, on the new compounds of the present invention surprisingly has been found to substantially increase the therapeutic efficacy of the compounds with respect to the treatment of *Pneumocystis carinii* pneumonia. Such new imidazoline compounds are represented specifically by Formula VI or preferably by the para-imidazoline structure of Subformula VIa:

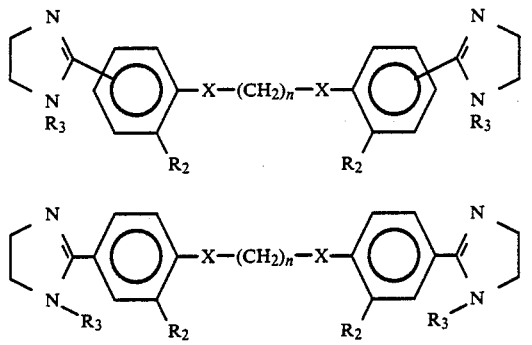

wherein $R_2$ is H, $OCH_3$, $NH_2$ or $NO_2$; $R_3$ is H, $CH_3$ or $CH_2CH_3$, X is O, N or S; and n=2, 3, 4 or 5 provided that when $R_2$ is H, n does not equal 5. The most preferred compound is represented by Subformula VIa when $R_2=OCH_3$, $R_3=H$, X=O, and n=3.

One especially important aspect of the present invention is the provision of a method for treating *Pneumocystis carinii* pneumonia. This method comprises administering to a patient suffering from *Pneumocystis carinii* pneumonia, a therapeutically effective amount of a compound of Formula I or a pharmaceutically acceptable salt thereof. Heretofore, pentamidine was one of only a few compounds of a structure similar to the structure to the compounds of Formula I that has been known to be effective in the treatment of, or prophylaxis against *Pneumocystis carinii* pneumonia. The only other diamidines known to have some effectiveness against PCP are dibromopropamidine, stilbamidine and hydroxystilbamidine.

Obviously, the therapeutically effective dosage of any specific compound, the use of which is in the scope of present invention, will vary somewhat from compound to compound and patient to patient. As a general proposition, a dosage from about 0.1 to about 20 mg/kg will have therapeutic efficacy. However, toxicity concerns at the higher level may restrict the dosage to a lower level such as up to about 10 mg/kg, all weights being calculated based upon the weight of the active base, including the cases where a salt is employed. Typically a dosage from about 0.5 mg/kg to about 5 mg/kg will be employed. The duration of the treatment is usually once per day for a period of two to three weeks or until the *Pneumocystis carinii* pneumonia is essentially controlled. Lower doses given less frequently can be used to prevent or reduce the incidence of recurrence of the infection.

In accordance with the present method, a compound of Formula I, or a pharmaceutically acceptable salt thereof, may be administered orally or through inhalation as a solid, or may be administered orally, through inhalation, intramuscularly, or intravenously, as a solution, suspension, or emulsion. Alternatively, the compound or salt may also be administered by inhalation, intravenously or intramuscularly as a liposomal suspension. When administered through inhalation the compound or salt should be in the form of a plurality of solid particles or droplets having a particle size from about 0.5 to about 5 microns, preferably from about 1 to about 2 microns.

Besides providing a method for treating *Pneumocystis carinii* pneumonia, the also provides a method for prophylaxis against *Pneumocystis carinii* pneumonia in an immunocompromised patient, such as one suffering from AIDS, who has had at least one episode of *Pneumocystis carinii* pneumonia, but who at the time of treatment is not exhibiting signs of pneumonia. As pneumocistis *carinii* pneumonia is an especially potentially devastating disease for immunocompromised patients it is preferable to avoid the onset of *Pneumocystis carinii* pneumonia, as compared to treating the disease after it has become symptomatic. Accordingly, the present invention provides a method for the prophylaxis against *Pneumocystis carinii* pneumonia comprising administering to the patient a prophylactically effective amount of a compound of Formula I (and preferably of Subformula Ia) or a pharmaceutically acceptable salt thereof. The forms for administration of the compound or salt in accordance with this method may be the same as utilized for the purpose of actually treating a patient suffering from *Pneumocystis carinii* pneumonia.

An additional useful aspect of the present invention is a method for prophylaxis against even an initial episode of *Pneumocystis carinii* pneumonia in an immunocompromised patient who has never experienced an episode of *Pneumocystis carinii* pneumonia. In this respect, a patient who has been diagnosed as being immunocompromised, such as one suffering from AIDS or ARC (AIDS related complex), even before the onset of an initial episode of *Pneumocystis carinii* pneumonia, may avoid or delay suffering from the infection by having administered a prophylactically effective amount of a compound of Formula I (or preferably of Formula Ia) or a pharmaceutically acceptable salt thereof. The compound or salt may be administered in the same fashion as in the treatment of patients suffering from *Pneumocystis carinii* pneumonia.

The present invention also provides new pharmaceutical compositions suitable for intravenous or intramuscular injection. The pharmaceutical compositions comprise a compound of Formula II (and preferably of Subformula IIa), or a pharmaceutically acceptable salt thereof, in any pharmaceutically acceptable carrier. If a solution is desired, water is the carrier of choice with respect to water-soluble compounds or salts. With respect to the water-insoluble compounds or salts, an organic vehicle, such as glycerol, propylene glycol, polyethylene glycol, or mixtures thereof, may be suitable. In the latter instance, the organic vehicle may contain a substantial amount of water. The solution in either instance may then be sterilized in any suitable manner, preferably by filtration through a 0.22 micron filter. Subsequent to sterilization, the solution may be filled into appropriate receptacles, such as depyrogenated glass vials. Of course, the filling should be done by an aseptic method. Sterilized closures may then be placed on the vials and, if desired, the vial contents may be lyophilized.

In addition to compounds of Formula II (and preferably of Subformula IIa) or their salts, the pharmaceutical compositions may contain other additives, such pH adjusting additives. In particular, useful pH adjusting agents include acids or bases or buffers, such a sodium lactate, sodium acetate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

In yet another aspect of the present invention, there is provided an injectable, stable, sterile composition comprising a compound of Formula II (and preferably of Subformula IIa), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into man. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

In accordance with the present invention, other pharmaceutical compositions may be prepared from the water-insoluble compounds of Formula II (and preferably of Subformula IIa), or salts thereof, such as aqueous based emulsions. In such an instance, the composition will contain a sufficient amount of a pharmaceutically acceptable emulsifying agent to emulsify the desired amount of the compound of Formula II (and preferably of Subformula IIa) or salt thereof. Particularly useful emulsifying agents include phosphatidyl cholines, and lecithin.

Further, the present invention provides liposomal formulations of the compounds of Formula II (and preferably of Subformula IIa) and salts thereof. The technology for forming liposomal suspensions is well known in the art. When the compound of Formula II or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds of Formula II or salts thereof, may be lyophilized to produce a lyophilizate which may be reconstituted with a pharmaceutically acceptable carrier, such as water, to regenerate a liposomal suspension.

In another aspect of the present invention, pharmaceutical formulations are provided which are suitable for administration as an aerosol, by inhalation. These formulations comprise a solution or suspension of the desired compound of Formula II (and preferably of Subformula IIa) or a salt thereof or a plurality of solid particles of the compound or salt. The desired formulation may be placed in a small chamber and nebulized. Nebulization may be accomplished by compressed air or by ultrasonic energy to form a plurality of liquid droplets or solid particles comprising the compounds or salts. The liquid droplets or solid particles should have a particle size in the range of about 0.5 to about 5 microns. The solid particles can be obtained by processing the solid compound of Formula II, or a salt thereof, in any appropriate manner known in the art, such as by micronization. Most preferably, the size of the solid particles or droplets will be from about 1 to about 2 microns. In this respect, commercial nebulizers are available to achieve this purpose.

Preferably, when the pharmaceutical formulation suitable for administration as an aerosol is in the form of a liquid, the formulation will comprise a water-soluble compound of Formula II (and preferably of Subformula IIa) or a salt thereof, in a carrier which comprises water. A surfactant may be present which lowers the surface tension of the formulation sufficiently to result in the formation of droplets within the desired size range when subjected to nebulization.

As indicted, the present invention provides both water-soluble and water-insoluble compounds and salts. As used in the present specification, the term "water-soluble" is meant to define any composition which is soluble in water in an amount of about 50 mg/mL, or greater. Also, as used in the present specification, the term "water-insoluble" is meant to define any composition which has solubility in water of less than about 20 mg/mL. For certain applications, water soluble compounds or salts may be desirable whereas for other applications water-insoluble compounds or salts likewise may be desirable.

The compounds employed in the present invention, whether known compounds or novel compounds, may be synthesized in manners generally known and readily understood by those skilled in the art. Therefore, there is no need to explain in great detail the methodology used for the synthesis of most of those compounds. The following summary of the synthesis routes as employed is an aid to those skilled in the art in choosing the appropriate known synthesis procedure to employ for the respective classes of compounds.

In general, the several reaction schemes which may be employed to synthesize the compounds of the present invention are shown in Charts I-III. As shown in Chart I, the compounds of Formula I in which $n=2-5$ (and for comparative purposes when $n=6$), $R_1=H$, $X=O$, and $R_2=H$ or $OCH_3$ may be prepared by alkylation of cyanophenol (with methoxy substitution when appropriate) with dibromoalkanes, to yield the corresponding cyano analogues to the compounds of Formula II, employing generally the procedure of Geratz et al., J. Med. Chem. 16: 970, 1973. The cyano analogue may then be subjected to Pinner's amidine synthesis to yield the desired products. Additionally, the imidate which is also obtained through the aforementioned alkalation reaction may be refluxed with ethylene diamine to yield the imidazoline products of the present invention which are represented by Formula I when two $R_1$ groups on an amidine group together represent $-CH_2CH_2-$. Further, the cyano compounds obtained as a result of the aforementioned alkylation reaction may be further reacted by nitrating said compounds using acetyl nitrate in trifluoroacetic acid, resulting in dinitrodicyano compounds which then may be converted to the corresponding amidines, using the aforementioned Pinner's amidine synthesis. The dinitrodiamidine compounds which result may be investgated for comparative purposes. Those dinitrodiamidine compounds may be further converted through catalytic reduction with $H_2$ and Pd/C to yield the corresponding diaminodiamidines useful in accordance with the present invention.

As shown in Chart II, the diazo derivatives which are represented by Formula I wherein $X=N$ and $R_2=H$ may be synthesized through a nucleophilic displacement reaction of 4-fluorobenzonitrile with diaminoalkanes, followed by the Pinner's amidine synthesis. Similarly, 4-chloro-3-nitrobenzonitrile may be reacted with diamino alkanes to yield the corresponding cyano derivative. Conversion of that intermediate to the final product is then dependent upon the relative solubilities. In this respect reference is made to Chart III which shows the synthesis of the compound wherein $X=N$, $R_2=NH_2$ and $n=2$, by reaction of 4-chloro-3-nitrobenzonitrile with a ten-fold excess of ethylene diamine at 25° C. to yield the corresponding mono-derivative which then may be catalytically reduced to form the corresponding amine, followed by a second nucleophilic displacement reaction with 4-chloro-3-nitrobenzonitrile to yield the corresponding dicyanomonoaminomononitrile which may then be subjected to Pinner's amidine synthesis and a final reduction to yield the desired diaminodiamidine product.

The compounds of Formula I wherein $X=N$ and $R_2=NH_2$, with $n=4$ or 6 likewise present a synthesis issue in that the intermediate cyano derivative obtained through the reaction of 4-chloro-3-nitrobenzonitrile with the corresponding diamino. alkanes results in an intermediate which is not soluble in any appropriate solvent for conversion to the corresponding diamidine derivative. In such an instance, the nitro groups may be reduced to amino groups and then converted to the desired diamidines, as depicted in route 2 on Chart II. The otherwise identical compounds, but wherein $n=3$ or 5, are slightly soluble in dioxane and therefore capable of being converted to diamidines directly, before reduction of the nitro groups to yield the final desired diaminodiamidine compounds.

As indicated, the compounds used in the present invention may be present as pharmaceutically acceptable salts. Such salts include the gluconate, lactate, acetate, tartarate, citrate, phosphate, borate, nitrate, sulfate, and hydrochloride salts.

The salts of the present invention may be prepared, in general, by reacting the amidine base compound with slightly in excess of two equivalents of the desired acid, in solution. After the reaction is complete, the salts are crystallized from solution by the addition of an appropriate amount of solvent in which the salt is insoluble.

The present invention will be further illustrated by the following non-limiting examples.

EXAMPLES 1-44

(Including comparative examples)

Compounds having the structure represented by Formula I were synthesized in accordance with the appropriate procedures discussed previously. The reaction schemes shown in Charts I-III specifically identify the methodology used to synthesize the compounds of the respective examples. The compounds which were synthesized are shown in Table IA and the elemental analysis and melting points of the compounds are shown in Table IB. Most of the compounds were tested for toxicity in rats using standard laboratory procedure and the results of that toxicity testing are shown in Table XII. The compounds of Examples 31, 32, and 34 were not synthesized but may be synthesized in the general manner discussed previously.

TESTING OF THE COMPOUNDS FOR THERAPEUTIC EFFICACY AGAINST PNEUMOCYSTIS CARINII

Induction and Treatment Of *Pneumocystis Carinii* in Sprague-Dawley Rats

Male Sprague-Dawley rats, barrier raised, non-certified virus free, weighing 150-200g were obtained from Hilltop Laboratories and housed individually. Animals were begun on a low (8%) protein diet (ICN Biomedicals, Cincinnati, OH) and drinking water containing tetracycline (0.5 mg/ml) and dexamethasone (1.0 $\mu$g/ml) immediately upon arrival. This treatment was given for the next 8 weeks, monitoring fluid intake daily and weighing animals weekly. Dilutions of the drinking solution were made when animals consumed too much fluid so as to prevent cortisone poisoning. At the beginning of the sixth week, animals were divided into groups of 8 animals each and the test compounds were administered daily by i.v. injection at a dose of 10 mg/kg, unless otherwise noted, for the next 14 days.

Animals were sacrificed at the end of the eighth week by chloroform inhalation and the left lung was removed aseptically and placed in sterile Hank's balanced salts solution without calcium or magnesium (HBSS-) for the ground tissue procedure. The right lung was inflated in situ with 10% formula and removed for histologic examination GMS staining.

Tissue processing procedure

Rat lungs not immediately processed were quickly frozen and stored at $-70°$ C. Tissues were removed from the freezer when ready for processing and quickly defrosted in a 25° C. waterbath. The lungs were then cut into small pieces and ground through a #60 wire mesh with a glass pestle. The minced lungs were suspended in 10ml of HBSS- and vortexed for 30 seconds. The suspension was centrifuged at 60 X g for 10 minutes, discarding the pellet and transferring the supernatant fluid to another tube and centrifuging at 150 X g for 10 minutes to remove the remaining cellular debris. The supernatant from this centrifugation was then spun at 10,000 X g for 10 minutes to pellet the *Pneumocystis* organisms. This pellet was resuspended in 2 ml of HBSS- for staining. Slides were prepared by placing a 10 ul drop of lung suspension on a clean microscope slide and allowing the drop to air dry. The slides were then stained with cresyl echt violet (Kodak Chemicals, Rochester, NY) to demonstrate the cyst form of the organism.

Statistical Studies

A total of 20 high power microscopic fields were counted for each lung suspension and the mean number of cysts was calculated.

RESULTS OF EXPERIMENTS

Table II

One compound useful in the treatment of PCP in accordance with the present invention, Example 4, was tested in comparison with pentamidine in both the normal para-form as well as the meta-form. The compound of Example 4 differed from pentamidine (para) in that the group linking the two aromatic nuclei was a —$(CH_2)_3$— group rather than the —$(CH_2)_5$— group of pentamidine. The compound of Example 4 was found better at controlling the extent of the pcp infection than either para- or meta- pentamidine.

Table III

Two novel compounds of the present invention having the structure of Formula II (and of Subformula IIa) wherein the structure differs from that of pentamidine in one instance because $R_2$ is a methoxy group and in the other instance because $R_2$ is an amino group (Example 15 and 14, respectively) were tested in comparison with pentamidine. Also included in the study was a known compound wherein the structure differed from that of pentamidine in that n is 6, representing then hexamidine (Example 20). Surprisingly, it was found that all three variations in structure from that of pentamidine resulted in improved performance in treating pcp.

Table IV

A compound of Formula I (and of Subformula Ia), butamidine (Example 9), was compared with pentamidine and two analogues thereof, the first within the scope of Formula II (and of Subformula IIa) wherein $R_2$ represents $NH_2$ (example 19) and the second within the scope of both Formulae I (and of Subformula Ia) and II (and of Subformula IIa) wherein $R_2=NO_2$ In the case of the amino substituted compound (Example 19), the etheric oxygens of pentamidine (position X) were also replaced by nitrogen. Of great surprise was the finding that the butamidine was significantly better than pentamidine in controlling pcp. Both of the other compounds were better than the control but were not as good as pentamidine in controlling pcp.

Table V

Four compounds of Formula II (and of Subformula IIa, Examples 7, 8, 17, and 18) similar to pentamidine with $n=3-5$, but having N in place of O (position X) were tested in comparison to pentamidine and derivatives in which the chain length of the bridging group was $n=6$, resulting in high toxicity. The new compound with nitro substitution ($n=5$, Example 18) was better than the control but was less effective than pentamidine, while the new compounds of examples 7, 8, and 17 were better than or equal to pentamidine, with the $n=3$ compound (Example 7) being most effective and the $n=5$ compound (Example 17) being the least effective. Then $n=6$ derivatives were comparable to pentamidine but had toxicity concerns (See Table XIII).

Table VI

Four novel compounds of Formula II (and Subformula IIa, Examples 3, 5, 10, and 14) were tested in comparison with pentamidine, with respect to their effectiveness in treating *Pneumocystis carinii* pneumonia, the compounds all having amino ($NH_2$) substitution on the aromatic nuclei, as shown in Formula II (and Subformula IIa) wherein $R_2=NH_2$. Further, in all instances the group linking the aromatic nuclei contained two etheric oxygens, as represented when $X=O$. The chain length of the bridging alkyl group was varied from 2 through 5 and for comparative purposes an additional compound, otherwise identical to the compounds within Formula II, was employed wherein the alkyl chain length was 6 (as represented when $n=6$). The compounds within the scope of Formula II (and Subformula IIa) were all significantly better than the control with respect to the treatment *Pneumocystis carinii* pneumonia and were approximately comparable to pentamidine in efficacy. The compound of example 22 wherein $n=6$ was significantly less effective than the other compounds or pentamidine in treating *Pneumocystis carinii* pneumonia and was toxic, see Table XIII.

Table VII

For comparative purposes, pentamidine and four analogues wherein the amidine group was in the meta position were analyzed for efficacy in treating *Pneumocystis carinii* pneumonia. The meta-amidine analogues had linking groups varying in carbon chain length from 3 to 6, as shown when $n=3-6$. Although none of the meta amidines functioned as well as parapentamidine with respect to therapeutic efficacy, they were all better than the control. Especially of interest is the fact that the meta- compounds having the shorter chain-length bridging groups ($a=3,4$) were better than the meta-form of pentamidine. Also for comparative purposes, a blocked amidine, otherwise identical to pentamidine was employed and found to be comparable to or perhaps slightly better than pentamidine with respect to therapeutic efficacy and treating pentamdine.

Table VIII

Three compounds within Formula II (and Subformula IIa, Examples 6, 11 and 15) containing methoxy groups were compared at 5 mg/kg to pentamidine with respect to therapeutic efficacy in treating *Pneumocystis carinii* pneumonia. Said compounds are represented in Formula II (and Subformula IIa) when $R_2=OCH_3$. Further, those specific compounds contained oxygen in the group bridging the two aromatic nuclei, as shown in Formula II when $X=O$. The length of the bridging carbon chain varied from 3 through 5 as shown when $n=3-5$. Also included in the study were two compounds wherein chlorine atoms were substituted on the aromatic nuclei, as would be represented by Formula IIa if $R_2=Cl$, which were slightly better than the control but much worse at a dose of 2.5 mg/kg than pentamidine in treating *Pneumocystis carinii* pneumonia. The compounds containing the methoxy group were significantly better, at one half the dose, than the control and, depending on chain length, worse than, equal to, or significantly better than pentamidine in treating *Pneumocystis carinii* pneumonia, at one half the dose of pentamidine. The shorter the chain length ($n=3$) the better the efficacy for such methoxy substituted compounds, with efficacy diminishing with increased chain length.

Table IX

Four compounds within the scope of Formula II (Examples 33, 41, 42, and 44) were compared against pentamidine with respect to therapeutic efficacy in treating *Pneumocystis carinii* pneumonia. In one instance (Example 33) the novel compound of the present invention contained an amino substituent on the aromatic nuclei ($R_2=NH_2$) and had nitrogen atoms in the group bridging the two aromatic nuclei ($X=N$), with short bridging alkyl chain length ($n=2$). That compound was better than the control, but worse than pentamidine. Three compounds wherein the amidine nitrogen groups had been linked through an ethylene bridge, to produce imidazolines were also compared at 2.5 mg/kg (Examples 41, 42, and 44). The compound of Example 44 having methoxy substitution on the aromatic nuclei ($R_2=OCH_3$) and as the group bridging the aromatic nuclei, —O(CH$_2$)$_3$O—, as represented when X=O and n=3, was found to be very effective in treating *Pneumocystis carinii*, being much better than pentamidine at only one fourth the dose. Two similar compounds were also tested which had methyl substituents on the imidazoline groups. The presence of such methyl groups were found to significantly decrease efficacy of the compound, while still being better than the control. Compound 44 represents the most preferred embodiment of the present invention in that the efficacy in treating *Pneumocystis carinii* pneumonia is very good at one fourth the dose level of pentamidine.

Table X

Six new compounds within the scope of Formula IIa (Examples 35, 36 37, 38, 40 and 43) were tested for therapeutic efficacy against *Pneumocystis carinii* pneumonia. Two new compounds (Examples 36 and 37) had amino substitution (R$_2$=NH$_2$) on the aromatic nuclei, along with nitrogen atoms in the group bridging the aromatic nuclei (X=N). Those compounds were compared to similar new compounds in which the substituents on the aromatic nuclei were nitro groups (Examples 35 — tested at 5 mg/kg — and 38 — tested at 2.5 mg/kg), the chain length of the bridging group being varied from 3 to 4 (n=3-4). The amino subsituted compounds were found to be better than the nitro substituted compounds, although the amino substituted compounds were tested at a higher dosage level. Also, two compounds within Formula IIa (Examples 40 and 43) having imidazoline groups (wherein two R$_1$ groups equal —CH$_2$CH$_2$—) were tested, one compound (Example 43) having methoxy substitution on the aromatic nuclei (R$_2$=OCH$_3$), with the group bridging the aromatic nuclei being —O(CH$_2$)$_5$O— and in the other instance (Example 40) no substitution on the aromatic nuclei, with the bridging group being —O(CH$_2$)$_4$O—. Both such novel compounds were found to be significantly better than the control, even though the compound of Example 43 was tested at a lower level of 5 mg/kg.

Table XI

To compare the efficacy of butamidine (R$_1$=H, R$_2$=H, X=0, n=5) against pentamidine, a logarithmic comparison was undertaken wherein both butamidine and pentamidine were tested for efficacy against *Pneumocystis carinii* pneumonia at dosages of 10 mg/kg, 1 mg/kg and 0.1 mg/kg. The butamidine was significantly better than pentamidine at the 10 mg/kg dosage level, confirming the results reported earlier in Table IV. However, when the dosage level was reduced to 1 mg/kg or 0.1 mg/kg, there was essentially no difference in the two compounds.

Summary

The composite results of the foregoing in vivo testing is set forth in Table XII. Although such compilations are of somewhat uncertain significance due to variations in control results from experiment to experiment, it still serves as a useful tool and fully summarizes the utility of the present invention.

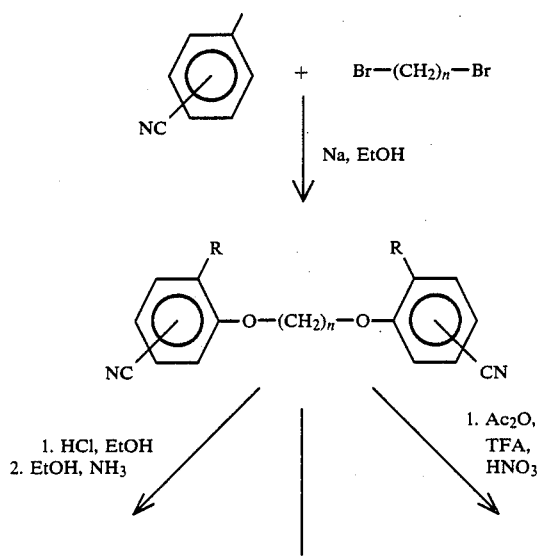

-continued
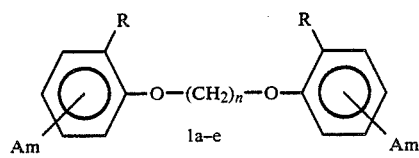
1,4,6,9,11,12,15,16,20, & 24-29
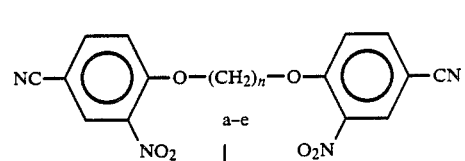
1. HCl, EtOH
2. NH₃, EtOH
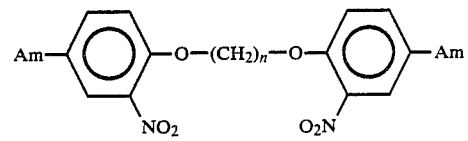
2,13,21,34, & 38
1. HCl, EtOH
2. NH₂—(CH₂)₂—NH₂
H₂, Pd/C
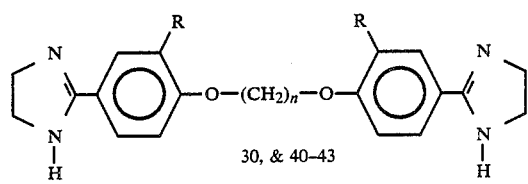
30, & 40-43
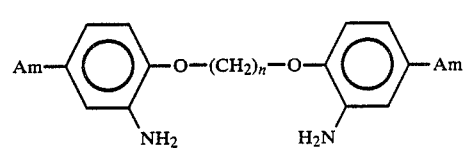
3,5,10,14, & 22
a = (n = 2)
b = (n = 3)
c = (n = 4)
d = (n = 5)
e = (n = 6)
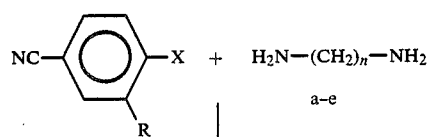
Et₃N, DMSO
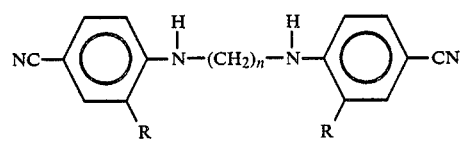

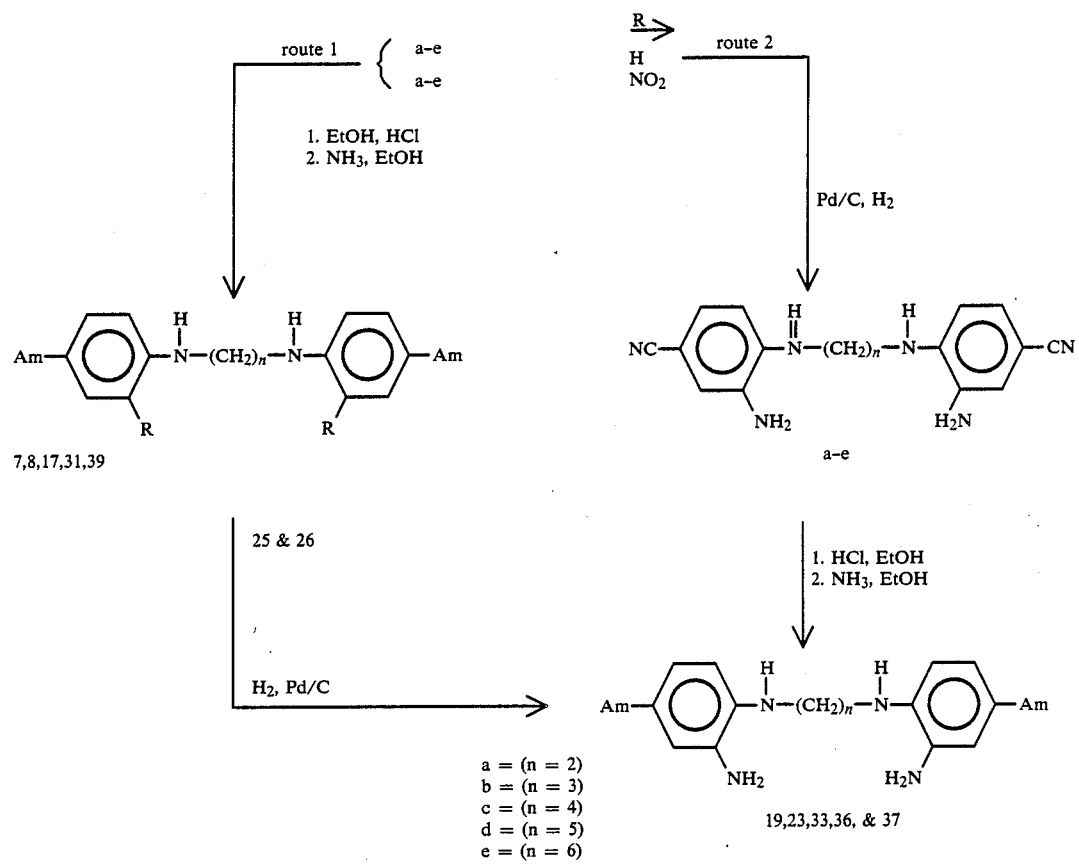
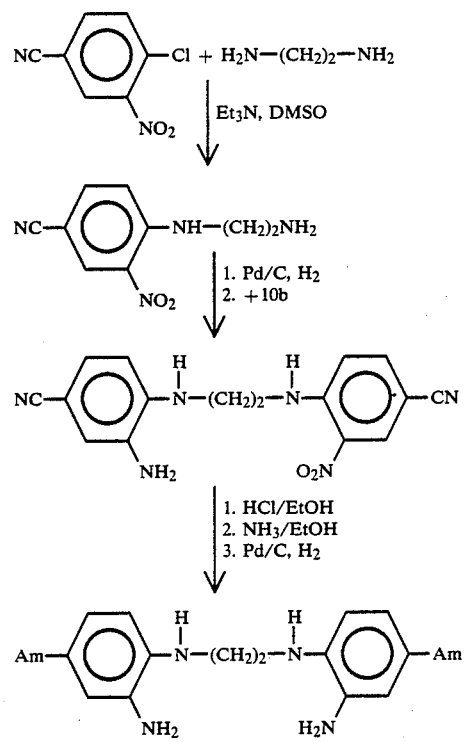
| # | X | n | R₂ |
|---|---|---|---|
| 1. | O | 2 | H |
| 2. | O | 2 | NO₂ |
| 3. | O | 2 | NH₂ |
| 4. | O | 3 | H |
| 5. | O | 3 | NH₂ |
| 6. | O | 3 | OCH₃ |
| 7. | N | 3 | H |
| 8. | N | 4 | H |
| 9. | O | 4 | H |
| 10. | O | 4 | NH₂ |
| 11. | O | 4 | OCH₃ |
| 12. | O | 5 | H |
| 13. | O | 5 | NO₂ |
| 14. | O | 5 | NH₂ |
| 15. | O | 5 | OCH₃ |
| 16. | O | 5 | Br |
| 17. | N | 5 | H |
| 18. | N | 5 | NO₂ |
| 19. | N | 5 | NH₂ |
| 20. | O | 6 | H |
| 21. | O | 6 | NO₂ |
| 22. | O | 6 | NH₂ |
| 23. | N | 6 | NH₂ |
| 24. | O | 4 | Cl |
| 25. | O | 5 | Cl |

TABLE IA-continued

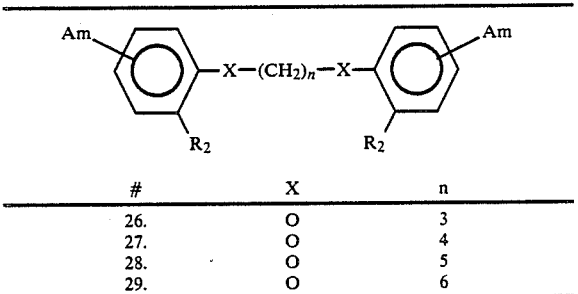

| # | X | n |
|---|---|---|
| 26. | O | 3 |
| 27. | O | 4 |
| 28. | O | 5 |
| 29. | O | 6 |

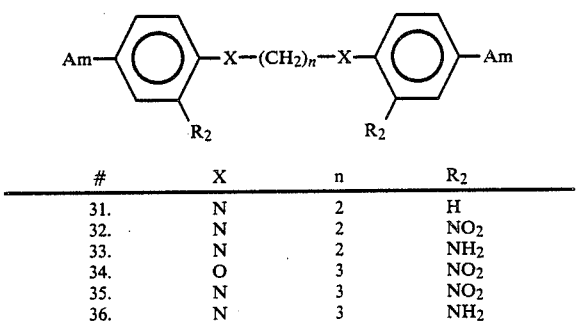

| # | X | n | R₂ |
|---|---|---|----|
| 31. | N | 2 | H |
| 32. | N | 2 | NO₂ |
| 33. | N | 2 | NH₂ |
| 34. | O | 3 | NO₂ |
| 35. | N | 3 | NO₂ |
| 36. | N | 3 | NH₂ |

TABLE IA-continued

| | | | |
|---|---|---|---|
| 37. | N | 4 | NH₂ |
| 38. | O | 4 | NO₂ |
| 39. | N | 6 | H |

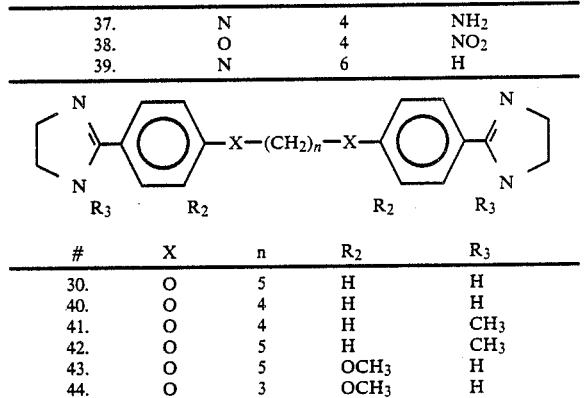

| # | X | n | R₂ | R₃ |
|---|---|---|----|----|
| 30. | O | 5 | H | H |
| 40. | O | 4 | H | H |
| 41. | O | 4 | H | CH₃ |
| 42. | O | 5 | H | CH₃ |
| 43. | O | 5 | OCH₃ | H |
| 44. | O | 3 | OCH₃ | H |

TABLE IB

ELEMENTAL ANALYSIS AND MELTING POINTS OF EXAMPLES 1–44

| Cmpd. Number | Analyzed Formula | Calculated C | Calculated H | Calculated N | Found C | Found H | Found N | M.P. | Yield |
|---|---|---|---|---|---|---|---|---|---|
| 1 | $C_{16}H_{18}N_4O_2/2HCl$ | 49.14 | 5.72 | 14.33 | 49.18 | 5.75 | 14.28 | >300 | 6% |
| 2 | $C_{16}H_{16}N_6O_6/1.1HCl/1.3H_2O$ | 42.53 | 4.39 | 18.60 | 42.83 | 4.01 | 17.07 | 287 | 39% |
| 3 | $C_{16}H_{20}N_6O_2/4HCl/0.4H_2O$ | 39.92 | 5.19 | 17.46 | 40.21 | 5.46 | 17.08 | >300 | 26% |
| 4 | $C_{17}H_{20}N_4O_2/2HCl/1.3H_2O$ | 49.96 | 6.07 | 13.71 | 49.96 | 6.10 | 13.59 | Dec at 144–145 | 82% |
| 5 | $C_{17}H_{22}N_6O_2/4HCl/0.6E10H$ | 40.81 | 5.98 | 15.69 | 40.72 | 5.62 | 15.31 | Dec at 273 | 6% |
| 6 | $C_{19}H_{24}N_4O_4/2HCl$ | 51.24 | 5.88 | 12.58 | 51.04 | 5.91 | 12.50 | 293 | 76% |
| 7 | $C_{17}H_{22}N_6/2HCl$ | 53.27 | 6.31 | 21.92 | 53.11 | 6.39 | 21.96 | 298–300 | 22% |
| 8 | $C_{18}H_{24}N_6/2HCl/0.5H_2O$ | 53.20 | 6.70 | 20.68 | 53.04 | 6.73 | 20.54 | >300 | 43% |
| 9 | $C_{18}H_{22}N_4O_2/2HCl/0.4H_2O$ | 53.18 | 6.15 | 13.78 | 53.41 | 6.21 | 13.41 | >300 | 95% |
| 10 | $C_{18}H_{24}N_6O_2/4HCl/1H_2O$ | 41.55 | 5.81 | 16.15 | 41.64 | 5.84 | 16.08 | 285 | 18% |
| 11 | $C_{20}H_{26}N_4O_4/2HCl/1.2H_2O$ | 49.94 | 6.37 | 11.65 | 49.98 | 6.29 | 11.61 | 297–299 | 70% |
| 12 | $C_{19}H_{24}N_4O_2/2HCl/1H_2O$ | 52.90 | 6.54 | 12.99 | 52.66 | 6.29 | 12.92 | 247 | 86% |
| 13 | $C_{19}H_{22}N_6O_6/2HCl$ | 45.34 | 4.81 | 16.70 | 45.22 | 4.86 | 16.64 | 255 | 74% |
| 14 | $C_{19}H_{26}N_6O_4/4HCl/1.6H_2O$ | 41.86 | 6.14 | 15.42 | 41.83 | 6.12 | 15.37 | 270 | 40% |
| 15 | $C_{21}H_{28}N_4O_4/2HCl/2H_2O$ | 49.51 | 6.73 | 11.00 | 49.57 | 6.74 | 10.99 | 258–259 | 63% |
| 16 | $C_{19}H_{22}N_4O_2Br_2/2HCl/1H_2O$ | 38.73 | 4.45 | 9.51 | 38.84 | 4.64 | 9.46 | 254–255 | 58% |
| 17 | $C_{19}H_{26}N_{6}2HCl/1.33H_2O$ | 52.42 | 7.10 | 19.30 | 52.32 | 7.08 | 19.17 | 295 | 48% |
| 18 | $C_{19}H_{24}N_8O_4/2HCl/2H_2O$ | 42.71 | 5.76 | 20.12 | 43.08 | 5.41 | 20.07 | 293–294 | 39% |
| 19 | $C_{19}H_{28}N_8/4HCl/2H_2O$ | 41.47 | 6.59 | 20.36 | 41.60 | 6.55 | 20.42 | 300–303 | 16% |
| 20 | $C_{20}H_{26}N_4O_2/2HCl/2.5H_2O$ | 50.91 | 7.32 | 11.31 | 50.94 | 7.05 | 11.31 | 252 | 69% |
| 21 | $C_{20}H_{24}N_6O_6/2HCl$ | 46.43 | 5.07 | 16.24 | 46.51 | 5.05 | 16.14 | Dec at 287–288 | 35% |
| 22 | $C_{20}H_{28}N_6O_2/4HCl/0.6H_2O$ | 45.49 | 6.45 | 15.01 | 45.13 | 6.84 | 14.61 | Dec at 290 | 18% |
| 23 | $C_{20}H_{30}N_8/4HCl/1.7H_2O$ | 42.97 | 6.74 | 20.05 | 43.05 | 6.76 | 19.97 | Dec at 285 | 18% |
| 24 | $C_{18}H_{18}N_4O_2/4HCl$ | 46.18 | 4.74 | 11.97 | 46.17 | 4.79 | 11.90 | >300 | 43% |
| 25 | $C_{19}H_{20}N_4O_2/4HCl/1.1H_2O$ | 45.46 | 5.26 | 11.16 | 45.49 | 5.23 | 10.98 | 247–248 | 55% |
| 26 | $C_{17}H_{20}N_4O_2/2HCl/1.9H_2O$ | 48.67 | 6.20 | 13.35 | 48.64 | 6.24 | 13.31 | 300 | 42% |
| 27 | $C_{18}H_{22}N_2O_2/2HCl/1.8H_2O$ | 50.07 | 6.44 | 12.98 | 50.10 | 6.46 | 12.97 | 257 | 68% |
| 28 | $C_{19}H_{24}N_4O_2/2HCl$ | 55.21 | 6.34 | 13.55 | 55.47 | 6.51 | 13.15 | 133–134 | 51% |
| 29 | $C_{20}H_{26}N_4O_2/2HCl/0.3H_2O$ | 55.51 | 6.66 | 12.95 | 55.45 | 6.67 | 12.88 | 268 | 64% |
| 30 | $C_{23}H_{28}N_4O_2/2.2H_2O$ | 54.70 | 6.87 | 11.09 | 54.69 | 6.87 | 11.06 | 147 | 81% |
| 31 | Not Synthesized | | | | | | | | |
| 32 | Not Synthesized | | | | | | | | |
| 33 | $C_{16}H_{22}N_8/4HCl/1.6H_2O/0.4EtOH$ | 38.84 | 6.13 | 21.57 | 38.83 | 6.00 | 21.81 | >300 | 27% |
| 34 | Not Synthesized | | | | | | | | |
| 35 | $C_{17}H_{20}N_8O_4/2HCl/1H_2O$ | 41.56 | 4.92 | 22.81 | 41.71 | 4.89 | 22.73 | Dec at 295 | 58% |
| 36 | $C_{17}H_{24}N_8/4HCl/1.1H_2O/0.3EtOH$ | 40.66 | 6.20 | 21.55 | 40.29 | 6.29 | 21.21 | 229 | 10% |
| 37 | $C_{18}H_{26}N_8/4HCl$ | 43.21 | 6.04 | 22.40 | 43.30 | 6.09 | 22.36 | Dec at 274–275 | 27% |
| 38 | $C_{18}H_{20}N_6O_6/2HCl$ | 44.18 | 4.53 | 17.18 | 44.08 | 4.55 | 17.10 | 298 | 26% |
| 39 | $C_{20}H_{28}N_6/2HCl/0.3H_2O$ | 55.76 | 7.16 | 19.15 | 55.80 | 7.17 | 19.44 | 300 | 54% |
| 40 | $C_{22}H_{26}N_4O_2/2HCl/2.2H_2O$ | 53.81 | 6.65 | 11.41 | 53.80 | 6.70 | 11.36 | 249–250 | 76% |
| 41 | $C_{24}H_{30}N_4O_2/1HCl/1.5H_2O$ | 61.33 | 7.29 | 11.92 | 61.17 | 7.40 | 11.75 | 203–205 | 15% |
| 42 | $C_{25}H_{32}N_4O_2/2HCl/1H_2O$ | 58.71 | 7.09 | 10.95 | 58.73 | 7.16 | 10.88 | 203–204 | 19% |
| 43 | $C_{25}H_{32}N_4O_4/2HCl/2.5H_2O$ | 52.63 | 6.89 | 9.82 | 52.47 | 6.85 | 9.97 | 175 | 70% |
| 44 | $C_{23}H_{28}N_4O_4/1.75HCl/2.00H_2O$ | 52.69 | 6.49 | 10.69 | 52.59 | 6.38 | 10.46 | 252 | 62% |

TABLE II

Extent of Disease by Histologic Score

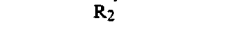

| Example No. | | | 0.5 | 1 | 2 | 3 | 4 |
|---|---|---|---|---|---|---|---|
| — | | Control | 0 | 1 | 2 | 1 | 4 |
| 12 | C | $R_2 = H, X = O, n = 5$, Amidine in para position | 1 | 5 | 2 | 0 | 0 |
| 4 | I | $R_2 = H, X = O, n = 3$, Amidine in para position | 3 | 4 | 1 | 0 | 0 |
| 28 | C | $R_2 = H, X = O, n = 5$, Amidine in meta position | 3 | 2 | 2 | 0 | 1 |

Histologic Scoring:
0.5 = <10 cysts found per 2 sections
1 = scattered cysts, <5% of lung involved
2 = scattered cysts, 5–10% lung involved or small foci of infection
3 = scattered cysts, 10–50% of lung involved with some intense areas of infection
4 = >50% of lung involved with many intense areas of focal infection
C = Comparative. I represents a known compound of Formula I and II represents a novel compound of Formula II

TABLE III

Extent of Disease by Histologic Score

| Example No. | | | 0.5 | 1 | 2 | 3 | 4 |
|---|---|---|---|---|---|---|---|
| — | | Control | 0 | 0 | 1 | 3 | 4 |
| 12 | C | $R_2 = H, X = O, n = 5$ | 0 | 3 | 4 | 1 | 0 |
| 20 | C | $R_2 = H, X = O, n = 6$ | 3 | 3 | 1 | 0 | 0 |
| 15 | II | $R_2 = OCH_3, X = O, n = 5$ | 2 | 1 | 3 | 0 | 0 |
| 14 | II | $R_2 = NH_2, X = O, n = 5$ | 2 | 4 | 1 | 1 | 0 |

Histologic Scoring:
0.5 = <10 cysts found per 2 sections
1 = scattered cysts, <5% of lung involved
2 = scattered cysts, 5–10% lung involved or small foci of infection
3 = scattered cysts, 10–50% of lung involved with some intense areas of infection
4 = >50% of lung involved with many intense areas of focal infection
C = Comparative. I represents a known compound of Formula I and II represents a novel compound of Formula II

TABLE IV

Extent of Disease by Histologic Score

| Example No. | | | 0.5 | 1 | 2 | 3 | 4 |
|---|---|---|---|---|---|---|---|
| — | | Control | 0 | 0 | 2 | 4 | 2 |
| 12 | C | $R_2 = H, X = O, n = 5$ | 4 | 4 | 0 | 0 | 0 |
| 9 | I | $R_2 = H, X = O, n = 4$ | 8 | 0 | 0 | 0 | 0 |
| 19 | II | $R_2 = NH_2, X = N, n = 5$ | 0 | 2 | 4 | 2 | 0 |

TABLE IV-continued

Extent of Disease by Histologic Score

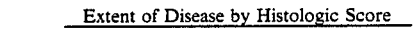

| Example No. | | | 0.5 | 1 | 2 | 3 | 4 |
|---|---|---|---|---|---|---|---|
| 13 | II | $R_2 = NO_2, X = O, n = 5$ | 3 | 2 | 3 | 0 | 0 |

Histologic Scoring:
0.5 = <10 cysts found per 2 sections
1 = scattered cysts, <5% of lung involved
2 = scattered cysts, 5–10% lung involved or small foci of infection
3 = scattered cysts, 10–50% of lung involved with some intense areas of infection
4 = >50% of lung involved with many intense areas of focal infection
C = Comparative. I represents a known compound of Formula I and II represents a novel compound of Formula II

TABLE V

Extent of Disease by Histologic Score

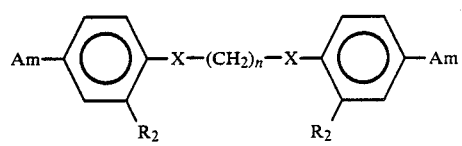

| Example No. | | | 0.5 | 1 | 2 | 3 | 4 |
|---|---|---|---|---|---|---|---|
| — | | Control | 1 | 1 | 3 | 1 | 2 |
| 12 | C | $R_2 = H, X = O, n = 5$ | 2 | 1 | 3 | 1 | 0 |
| 7 | II | $R_2 = H, X = N, n = 3$ | 5 | 1 | 2 | 0 | 0 |
| 8 | II | $R_2 = H, X = N, n = 4$ | 3 | 1 | 0 | 0 | 0 |
| 17 | II | $R_2 = H, X = N, n = 5$ | 1 | 2 | 3 | 1 | 0 |
| 39 | C | $R_2 = H, X = N, n = 6$ | 2 | 1 | 0 | 0 | 0 |
| 21 | C | $R_2 = NO_2, X = O, n = 6$ | 4 | 1 | 1 | 0 | 0 |
| 18 | II | $R_2 = NO_2, X = N, n = 5$ | 1 | 3 | 0 | 2 | 1 |
| 23 | C | $R_2 = NH_2, X = N, n = 6$ | 3 | 1 | 2 | 0 | 1 |

Histologic Scoring:
0.5 = <10 cysts found per 2 sections
1 = scattered cysts, <5% of lung involved
2 = scattered cysts, 5–10% lung involved or small foci of infection
3 = scattered cysts, 10–50% of lung involved with some intense areas of infection
4 = >50% of lung involved with many intense areas of focal infection
C = Comparative. I represents a known compound of Formula I and II represents a novel compound of Formula II

TABLE VI

Extent of Disease by Histologic Score

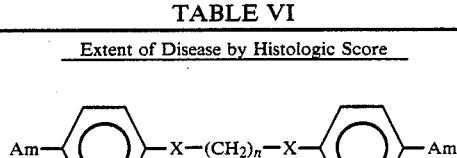

| Example No. | | | 0.5 | 1 | 2 | 3 | 4 |
|---|---|---|---|---|---|---|---|
| — | | Control | 0 | 0 | 0 | 4 | 4 |
| 12 | C | $R_2 = H, X = O, n = 5$ | 5 | 3 | 0 | 0 | 0 |
| 3 | II | $R_2 = NH_2, X = O, n = 2$ | 4 | 4 | 0 | 0 | 0 |
| 5 | II | $R_2 = NH_2, X = O, n = 3$ | 2 | 4 | 1 | 0 | 0 |
| 10 | II | $R_2 = NH_2, X = O, n = 4$ | 2 | 5 | 1 | 0 | 0 |
| 14 | II | $R_2 = NH_2, X = O, n = 5$ | 6 | 1 | 0 | 0 | 0 |

TABLE VI-continued

Extent of Disease by Histologic Score

Am—⬡—X—(CH₂)ₙ—X—⬡—Am
         |                    |
         R₂                   R₂

| Example No. | | | | NUMBER OF ANIMALS | | | | |
|---|---|---|---|---|---|---|---|---|
| | | | | 0.5 | 1 | 2 | 3 | 4 |
| 22 | C | R₂ = NH₂, X = O, n = 6 | | 0 | 1 | 4 | 3 | 0 |

Histologic Scoring:
0.5 = < 10 cysts found per 2 sections
1 = scattered cysts, < 5% of lung involved
2 = scattered cysts, 5–10% lung involved or small foci of infection
3 = scattered cysts, 10–50% of lung involved with some intense areas of infection
4 = > 50% of lung involved with many intense areas of focal infection
C = Comparative, I represents a known compound of Formula I and II represents a novel compound of Formula II

TABLE VII

Extent of Disease by Histologic Score

Am—⬡—X—(CH₂)ₙ—X—⬡—Am
         |                    |
         R₂                   R₂

| Example No. | | | | NUMBER OF ANIMALS | | | | |
|---|---|---|---|---|---|---|---|---|
| | | | | 0.5 | 1 | 2 | 3 | 4 |
| — | | Control | | 0 | 0 | 1 | 3 | 4 |
| 12 | C | Pentamidine | | 4 | 2 | 2 | 0 | 0 |
| 26 | I | n = 3, Am = meta | | 2 | 1 | 4 | 1 | 0 |
| 27 | I | n = 4, Am = meta | | 2 | 1 | 1 | 3 | 0 |
| 28 | C | n = 5, Am = meta | | 1 | 1 | 4 | 2 | 0 |
| 29 | C | n = 6, Am = meta | | 1 | 4 | 1 | 2 | 0 |
| — | I | n = 5, Am = blocked | | 5 | 3 | 0 | 0 | 0 |

Histologic Scoring:
0.5 = < 10 cysts found per 2 sections
1 = scattered cysts, < 5% of lung involved
2 = scattered cysts, 5–10% lung involved or small foci of infection
3 = scattered cysts, 10–50% of lung involved with some intense areas of infection
4 = > 50% of lung involved with many intense areas of focal infection
C = Comparative, I represents a known compound of Formula I and II represents a novel compound of Formula II

TABLE VIII

Extent of Disease by Histologic Score

Am—⬡—X—(CH₂)ₙ—X—⬡—Am
         |                    |
         R₂                   R₂

| Example No. | | | NUMBER OF ANIMALS | | | | |
|---|---|---|---|---|---|---|---|
| | | | 0.5 | 1 | 2 | 3 | 4 |
| — | | Control | 0 | 0 | 0 | 1 | 7 |
| 12 | C | R₂ = H, X = O, n = 5 | 4 | 2 | 0 | 0 | 0 |
| 6 | II | R₂ = OCH₃, X = O, n = 3 | 7 | 1 | 0 | 0 | 0 |
| 11 | II | R₂ = OCH₃, X = O, n = 4 | 3 | 4 | 1 | 0 | 0 |
| 15 | II | R₂ = OCH₃, X = O, n = 5 | 0 | 3 | 4 | 1 | 0 |
| 24 | C | R₂ = Cl, X = O, n = 4 | 0 | 1 | 2 | 3 | 2 |
| 25 | C | R₂ = Cl, X = O, n = 5 | 0 | 0 | 0 | 4 | 4 |

Histologic Scoring:
0.5 = < 10 cysts found per 2 sections
1 = scattered cysts, < 5% of lung involved
2 = scattered cysts, 5–10% lung involved or small foci of infection
3 = scattered cysts, 10–50% of lung involved with some intense areas of infection
4 = > 50% of lung involved with many intense areas of focal infection
C = Comparative, I represents a known compound of Formula I and II represnets a novel compound of Formula II

TABLE IX

Extent of Disease by Histologic Score

Am—⬡—X—(CH₂)ₙ—X—⬡—Am
         |                    |
         R₂                   R₂

| Example No. | | | NUMBER OF ANIMALS | | | | |
|---|---|---|---|---|---|---|---|
| | | | 0.5 | 1 | 2 | 3 | 4 |
| — | | Control | 0 | 0 | 0 | 6 | 2 |
| 12 | C | R₂ = H, X = O, n = 5 | 0 | 6 | 1 | 0 | 0 |
| 33 | II | R₂ = NH₂, X = N, n = 2 | 0 | 0 | 4 | 3 | 1 |

| | | —X—(CH₂)ₙ—X— | | | | | |
|---|---|---|---|---|---|---|---|
| | | R₃  R₂      R₂  R₃ | | | | | |
| 42 | II | R₃ = CH₃, R₂ = H, X = O, n = 5 | 0 | 0 | 2 | 3 | 3 |
| 41 | II | R₃ = CH₃, R₂ = H, X = O, n = 4 | 0 | 0 | 2 | 4 | 2 |
| 44 | II | R₃ = H, R₂ = OCH₃, X = O, n = 3 | 6 | 2 | 0 | 0 | 0 |

Histologic Scoring:
0.5 = < 10 cysts found per 2 sections
1 = scattered cysts, < 5% of lung involved
2 = scattered cysts, 5–10% lung involved or small foci of infection
3 = scattered cysts, 10–50% of lung involved with some intense areas of infection
4 = > 50% of lung involved with many intense areas of focal infection
C = Comparative, I represents a known compound of Formula I and II represents a novel compound of Formula II

TABLE X

Extent of Disease by Histologic Score

Am—⬡—X—(CH₂)ₙ—X—⬡—Am
         |                    |
         R₂                   R₂

| Example No. | | | NUMBER OF ANIMALS | | | | | |
|---|---|---|---|---|---|---|---|---|
| | | | 0.5 | 1 | 2 | 3 | 4 | |
| — | | Control | 0 | 0 | 1 | 2 | 5 | — |
| 35 | II | R₂ = NO₂, X = N, n = 3 | 0 | 0 | 0 | 2 | 6 | 5 mg/kg |

TABLE X-continued

| | | Extent of Disease by Histologic Score | | | | | | |
|---|---|---|---|---|---|---|---|---|
| 36 | II | $R_2 = NH_2, X = N, n = 3$ | 1 | 4 | 2 | 0 | 0 | 10 mg/kg |
| 37 | II | $R_2 = NH_2, X = N, n = 4$ | 0 | 4 | 3 | 1 | 0 | 10 mg/kg |
| 38 | II | $R_2 = NO_2, X = O, n = 4$ | 0 | 0 | 3 | 1 | 4 | 2.5 mg/kg |

| | | $-X-(CH_2)_n-X-$ | | | | | |
|---|---|---|---|---|---|---|---|
| | | | $R_3$ | $R_2$ | $R_2$ | $R_3$ | |
| 40 | II | $R_2 = H, R_3 = H, X = O, n = 4$ | 1 | 2 | 3 | 1 | 0 | 10 mg/kg |
| 43 | II | $R_3 = H, R_2 = OCH_3, X = O, n = 5$ | 1 | 3 | 1 | 2 | 0 | 5 mg/kg |

Histologic Scoring:
0.5 = < 10 cysts found per 2 sections
1 = scattered cysts, < 5% of lung involved
2 = scattered cysts, 5–10% lung involved or small foci of infection
3 = scattered cysts, 10–50% of lung involved with some intense areas of infection
4 = > 50% of lung involved with many intense areas of focal infection
C = Comparative, I represents a known compound of Formula I and II represents a novel compound of Formula II

TABLE XI

Extent of Disease by Histologic Score

| | NUMBER OF ANIMALS | | | | |
|---|---|---|---|---|---|
| | 0.5 | 1 | 2 | 3 | 4 |
| Control | 0 | 0 | 2 | 5 | 5 |
| Pentamidine 10 mg/kg | 3 | 5 | 2 | 1 | 0 |
| Butamidine 10 mg/kg | 10 | 2 | 0 | 0 | 0 |
| Pentamidine 1 mg/kg | 1 | 0 | 3 | 5 | 3 |
| Butamidine 1 mg/kg | 0 | 1 | 3 | 5 | 3 |
| Pentamidine 0.1 mg/kg | 0 | 0 | 0 | 7 | 5 |
| Butamidine 0.1 mg/kg | 0 | 0 | 4 | 5 | 2 |

Histologic Scoring:
0.5 = < 10 cysts found per 2 sections
1 = scattered cysts, < 5% of lung involved
2 = scattered cysts, 5–10% lung involved or small foci of infection
3 = scattered cysts, 10–50% of lung involved with some intense areas of infection
4 = > 50% of lung involved with many intense areas of focal infection

TABLE XII

EXTENT OF DISEASE BY HISTOLOGIC SCORE (COMBINED)

| Compound Number[b] | Number of Animals per Scoring Group @ | | | | |
|---|---|---|---|---|---|
| | 0.5 | 1 | 2 | 3 | 4 |
| Saline | 1 | 2 | 9 | 25 | 35 |
| 1. | Not tested in animals - insoluble | | | | |
| 2. | Not tested in animals - insoluble | | | | |
| 3. | 4 | 4 | 0 | 0 | 0 |
| 4. | 3 | 4 | 1 | 0 | 0 |
| 5. | 2 | 4 | 1 | 0 | 0 |
| 6.[c] | 7 | 1 | 0 | 0 | 0 |
| 7. | 5 | 1 | 2 | 0 | 0 |
| 8. | 3 | 1 | 0 | 0 | 0 |
| 9. | 8 | 0 | 0 | 0 | 0 |
| 10. | 2 | 5 | 1 | 0 | 0 |
| 11.[c] | 3 | 4 | 1 | 0 | 0 |
| 12. (Pentamidine) | 20 | 26 | 12 | 2 | 0 |
| 13.[c] | 0 | 2 | 4 | 2 | 0 |
| 14. | 8 | 5 | 1 | 1 | 0 |
| 15.[d] | 2 | 4 | 7 | 1 | 0 |
| 16. | Not tested in animals - insoluble | | | | |
| 17. | 1 | 2 | 3 | 1 | 0 |
| 18.[c] | 1 | 3 | 0 | 2 | 1 |
| 19. | 3 | 2 | 3 | 0 | 0 |
| 20. | 3 | 3 | 1 | 0 | 0 |
| 21.[e] | 4 | 1 | 1 | 0 | 0 |
| 22.[c] | 0 | 1 | 4 | 3 | 0 |
| 23. | 3 | 1 | 2 | 0 | 1 |
| 24.[d] | 0 | 1 | 2 | 3 | 2 |
| 25.[d] | 0 | 0 | 0 | 4 | 4 |
| 26. | 2 | 1 | 4 | 1 | 0 |
| 27. | 2 | 1 | 1 | 3 | 0 |
| 28. | 4 | 3 | 6 | 2 | 1 |
| 29. | 1 | 4 | 1 | 2 | 0 |
| 30. | 5 | 3 | 0 | 0 | 0 |
| 31. | Not tested in animals - synthesis in progress | | | | |
| 32. | Not tested in animals - synthesis in progress | | | | |
| 33. | 0 | 0 | 4 | 3 | 1 |
| 34. | Not tested in animals | | | | |
| 35.[c] | 0 | 0 | 0 | 2 | 6 |
| 36. | 1 | 4 | 2 | 0 | 0 |
| 37. | 0 | 4 | 3 | 1 | 0 |
| 38.[d] | 0 | 0 | 3 | 1 | 4 |
| 39. | Not tested in animals | | | | |
| 40. | 1 | 2 | 3 | 1 | 0 |
| 41.[d] | 0 | 0 | 2 | 4 | 2 |
| 42.[d] | 0 | 0 | 2 | 3 | 3 |
| 43.[c] | 1 | 3 | 1 | 2 | 0 |
| 44.[d] | 6 | 2 | 0 | 0 | 0 |

[a]Histologic Scoring:
0.5 = < 10 cysts found per 2 sections
1 = scattered cysts, < 5% of lung involved
2 = scattered cysts, 5–10% of lung involved
3 = scattered cysts, 10–50% of lung involved with some intense focal areas of infection
4 = > 50% of lung involved with many intense areas of focal infection
[b]All compounds were tested at 10 mg/kg unless otherwise indicated
[c]Tested at 5 mg/kg
[d]Tested at 2.5 mg/kg
[e]Tested at 1.25 mg/kg

TABLE XIII

TOXICITY OF AMIDINES

| Compound Number | Effect |
|---|---|
| 1. | Not tested in animals - insoluble |
| 2. | Not tested in animals - insoluble |
| 3. | None |
| 4. | Slight swelling at injection site |
| 5. | None |
| 6. | None - tested at 5 mg/kg only |
| 7. | None |
| 8. | Necrosis at tips of tails, chronic toxicity, 3 deaths by day 7 with 10 mg/kg |
| 9. | None |
| 10. | None |
| 11. | None - tested at 5 mg/kg only |
| 12. | Some hypotension, edematous tails |
| 13. | Acute toxicity,-death at 10 mg/kg |
| 14. | None |
| 15. | Severe hypotension, acute toxicity - death at 10 mg/kg |
| 16. | Not tested in animals - insoluble |
| 17. | Chronic toxicity - 2 deaths by day 13 with 10 mg/kg |
| 18. | Acute toxicity - death at 10 mg/kg |
| 19. | Tremors |
| 20. | Some hypotension, edematous tails, strong anticoagulant effect |
| 21. | Acute toxicity - death at 10, 5, and 2.5 mg/kg |
| 22. | Acute toxicity - death at 10 mg/kg |
| 23. | Spasms when injected rapidly |
| 24. | None - tested at 2.5 mg/kg due to solubility |

TABLE XIII-continued
TOXICITY OF AMIDINES

| Compound Number | Effect |
| --- | --- |
| 25. | None - tested at 2.5 mg/kg due to solubility |
| 26. | None |
| 27. | None |
| 28. | Slight swelling at injection site |
| 29. | Slightly edematous tails |
| 30. | None |
| 31. | Not tested |
| 32. | Not tested |
| 33. | Some anticoagulant effect |
| 34. | Not tested |
| 35. | Tested at 5 mg/kg due to solubility - no toxicity |
| 36. | None |
| 37. | None |
| 38. | Acute toxicity at 10 mg/kg and 5 mg/kg - tested at 2.5 mg/kg with no toxicity |
| 39. | Not tested in animals |
| 40. | None |
| 41. | Tested at 2.5 mg/kg due to solubility - no toxicity |
| 42. | Acute toxicity at 10 mg/kg and 5 mg/kg - tested at 2.5 mg/kg with no toxicity |
| 43. | Acute toxicity at 10 mg/kg, "quivers" and cardiac arrhythmias - tested at 5 mg/kg with no toxicity |
| 44. | Tested at 2.5 mg/kg due to solubility - no toxicity |

What is claimed is:

1. A compound having the following structural formula:

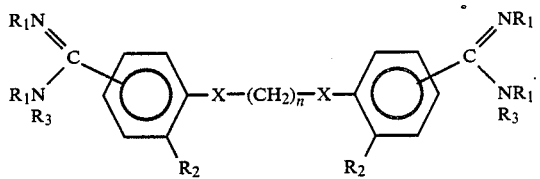

wherein each $R_1$ is H or two $R_1$ groups on the same amidine group together represent $-(CH_2)_m-$, wherein $m=2, 3,$ or $4$; $R_2$ is H, $OCH_3$, $NO_2$ or $NH_2$; $R_3$ is H, $CH_3$ or $CH_2CH_3$, $n=2,3,4,$ or $5$; and X is O, N, or S; provided that when X is O or S, both $R_2$ and both $R_3$ cannot be H.

2. A compound as defined in claim 1 having the following structure,

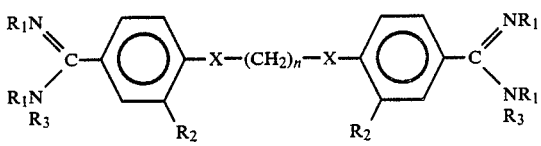

wherein $R_1$, $R_2$, $R_3$, X and n have the meanings of claim 1.

3. A compound of claim 1 having the following structure,

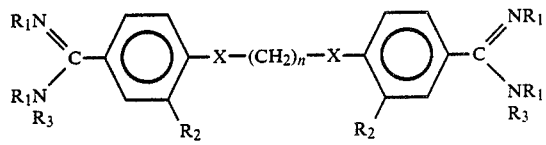

wherein each $R_1$ is H or two $R_1$ groups on the same amidine group together represent $-CH_2CH_2-$; $R_2$ is $OCH_3$, $NO_2$ or $NH_2$;

$R_3$ is H, $CH_3$, or $CH_2CH_3$;

X is O or N; and $n=2, 3, 4,$ or $5$.

4. A compound as defined in claim 1 having the following structure,

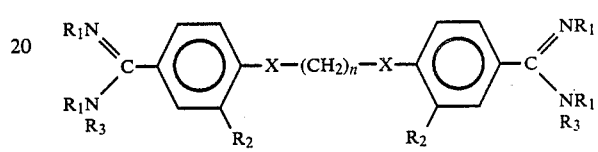

wherein each $R_1$ is H or two $R_1$ groups on the same amidine group together represent $-CH_2CH_2-$; $R_2$ is H, $OCH_3$, $NO_2$ or $NH_2$; and $n=2, 3, 4$ or $5$, and $R_3$ and X have the meanings of claim 1.

5. A compound of claim 1 having the following structure,

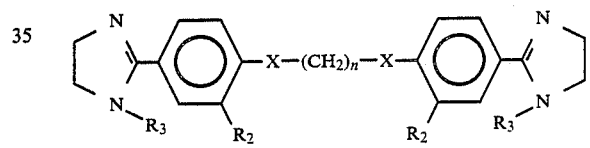

wherein $R_2$ is H, $OCH_3$, $NO_2$ or $NH_2$; is O or N; and $n=2, 3, 4$ and $5$ and $R_3$ has the meaning of claim 1, provided that when $R_2$ is H, n does not equal 5.

6. The compound of claim 5 wherein $R_2=OCH_3$, $R_3=H$, $X=O$, and $n=3$.

7. A pharmaceutical formulation comprising a therapeutically effective amount of a compound having the formula:

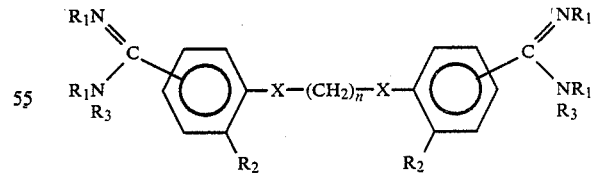

wherein each $R_1$ is H or two $R_1$ groups on the same amidine group together represent $-(CH_2)_m-$, wherein $m=2, 3,$ or $4$,; $R_2$ is H, $OCH_3$, $NO_2$ or $NH_2$; $R_3$ is H, $CH_3$ or $CH_2CH_3$, $n=2, 3, 4,$ or $5$; and X is O, N, or S; provided that when X is O or S, both $R_2$ and both $R_3$ cannot be H and a pharmaceutically acceptable carrier.

8. The pharmaceutical formulation of claim 7 wherein the compound has the following structure,

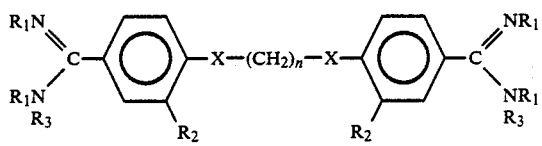

wherein $R_1$, $R_2$, $R_3$, X and n have the meanings of claim 7.

9. The pharmaceutical formulation of claim 7 wherein the compound has the following structure;

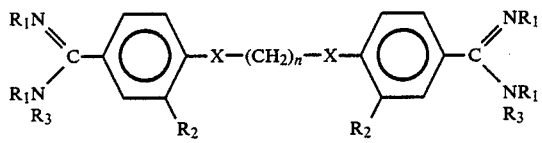

wherein each $R_1$ is H or two $R_1$ groups on the same amidine group together represent —$CH_2CH_2$—; $R_2$ is $OCH_3$, $NO_2$ or $NH_2$;

$R_3$ is H, $CH_3$, or $CH_2CH_3$;

X is O or N; and n=2, 3, 4, or 5.

10. The pharmaceutical formulation of claim 7 wherein the compound has the following structure,

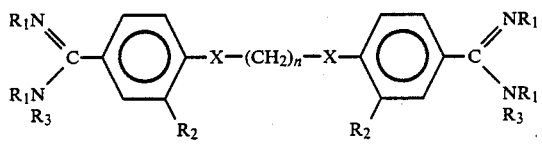

wherein each $R_1$ is H or two $R_1$ groups on the same amidine group together represent —$CH_2CH_2$—; $R_2$ is H, $OCH_3$, $NO_2$ or $NH_2$; and n=2, 3, 4 or 5, and $R_3$ and X have the meanings of claim 7.

11. The pharmaceutical formulation of claim 7 wherein the compound has the following structure,

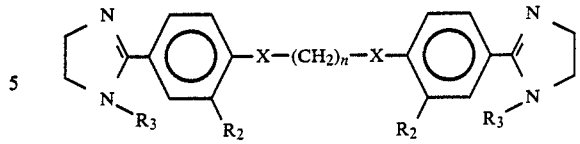

wherein $R_2$ is H, $OCH_3$, or $NH_2$; X is O or N; and n=2, 3, 4 or 5 and $R_3$ has the meaning of claim 7, provided that when $R_2$ is H, n does not equal 5.

12. The pharmaceutical formulation of claim 11 wherein $R_2$—$OCH_3$, $R_3$=H, X=O, and n=3.

13. A method for treating *Pneumocystis carinii* pneumonia comprising administering to a host suffering form *Pneumocystis carinii* pneumonia, a therapeutically effective amount of a compound of Formula I;

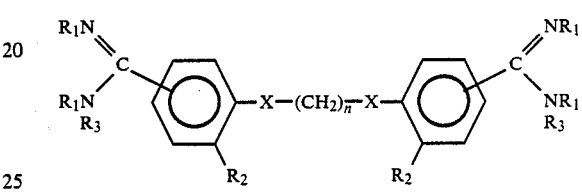

wherein each $R_1$ is H or two $R_1$ groups on the same amidine group together represent —$(CH_2)_m$—, wherein m=2, 3, or 4; $R_2$ is H, $OCH_3$, $NO_2$ or $NH_2$; $R_3$ is H, $CH_3$ or $CH_2CH_3$, N=2, 3, 4, or 5; and X is O, N, or S; provided that when X is O or S, both $R_2$ and both $R_3$ cannot be H.

14. A method for achieving prophylaxis against *Pneumocystis carinii* pneumonia comprising administering to a host at risk of suffering from *Pneumocystis carinii* pneumonia, a prophylactically effective amount of a compound of the formula:

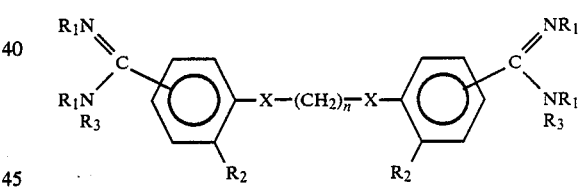

wherein each $R_1$ is H or two $R_1$ groups on the same amidine group together represent —$(CH_2)_m$—, wherein m=2, 3, or 4; $R_2$ is H, $OCH_3$, $NO_2$ or $NH_2$; $R_3$ is H, $CH_3$ or $CH_2CH_3$, n=2, 3, 4, or 5; and X is O, N, or S; provided that when X is O or S, both $R_2$ and both $R_3$ cannot be H.

* * * * *

UNITED STATES PATENT AND TRADEMARK OFFICE
CERTIFICATE OF CORRECTION

PATENT NO. : 4,933,347

DATED : June 12, 1990

INVENTOR(S) : Richard R. Tidwell, Dieter J. Geratz, Kwasi A. Ohemeng and James E. Hall It is certified that error appears in the above-identified patent and that said Letters Patent is hereby corrected as shown below:

Please insert in Column 1, line 6, after the title, and before "FIELD OF THE INVENTION":

"This invention was made with government support under N01-AI-72648 awarded by the National Institutes of Health. The government has certain rights in the invention."

Signed and Sealed this

Sixth Day of April, 1993

*Attest:*

STEPHEN G. KUNIN

*Attesting Officer*   Acting Commissioner of Patents and Trademarks